(12) United States Patent
Pawar et al.

(10) Patent No.: US 7,174,774 B2
(45) Date of Patent: Feb. 13, 2007

(54) METHOD AND APPARATUS OF DETECTING POOLING OF FLUID IN DISPOSABLE OR NON-DISPOSABLE ABSORBENT ARTICLES

(75) Inventors: Pau-Lin Pawar, Appleton, WI (US); Pete D. Honer, Larsen, WI (US); Frank F. Kromenaker, Appleton, WI (US); Michael J. Faulks, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 222 days.

(21) Appl. No.: 10/232,167

(22) Filed: Aug. 30, 2002

(65) Prior Publication Data

US 2004/0043369 A1 Mar. 4, 2004

(51) Int. Cl.
*G01N 5/02* (2006.01)

(52) U.S. Cl. .......................................... 73/73; 434/365

(58) Field of Classification Search ................ 434/262, 434/267, 261, 273; 340/573.5, 604; 607/41; 702/19, 50, 51, 55, 183; 703/11; 604/361; 73/73, 866.4, 38; 324/694, 696
See application file for complete search history.

(56) References Cited

U.S. PATENT DOCUMENTS

| | | | |
|---|---|---|---|
| 2,545,281 A * | 3/1951 | Hunt ............................... 73/73 |
| 3,190,038 A * | 6/1965 | Kardon ........................ 446/302 |
| 3,490,170 A * | 1/1970 | Wolf ............................ 446/192 |
| 3,952,584 A * | 4/1976 | Lichstein ......................... 73/73 |
| 4,360,345 A | 11/1982 | Hon |
| 4,541,439 A * | 9/1985 | Hon ............................. 600/504 |
| 4,842,595 A | 6/1989 | Nakanishi et al. |
| 5,009,651 A | 4/1991 | Kamishioiri et al. |
| 5,043,704 A * | 8/1991 | Blakeney ................. 340/573.5 |
| 5,264,830 A * | 11/1993 | Kline et al. .................. 340/604 |
| 5,356,403 A | 10/1994 | Faulks et al. |
| 5,392,032 A * | 2/1995 | Kline et al. .................. 340/604 |
| 5,509,810 A | 4/1996 | Schertz et al. |
| 5,557,263 A * | 9/1996 | Fisher et al. ................. 340/605 |
| 5,790,036 A * | 8/1998 | Fisher et al. ................. 340/605 |
| 5,853,292 A * | 12/1998 | Eggert et al. ................ 434/262 |
| 5,868,723 A * | 2/1999 | Al-Sabah ..................... 604/361 |
| 5,873,731 A | 2/1999 | Prendergast |
| 5,882,207 A | 3/1999 | Lampotang et al. |
| 5,890,908 A | 4/1999 | Lampotang et al. |
| 5,904,671 A * | 5/1999 | Navot et al. ................. 604/361 |
| 6,050,826 A | 4/2000 | Christianson et al. |
| 6,138,500 A * | 10/2000 | Steger et al. ................... 73/73 |
| 6,152,906 A | 11/2000 | Faulks et al. |

(Continued)

FOREIGN PATENT DOCUMENTS

EP 1047033 A1 * 10/2000

(Continued)

*Primary Examiner*—Kathleen Mosser
(74) *Attorney, Agent, or Firm*—Dority & Manning, P.A.

(57) ABSTRACT

A method and apparatus for detecting pooling of fluid in disposable or non-disposable absorbent articles is provided. The apparatus includes an object that has at least one surface area onto which pooling may occur. A fluid delivery apparatus is present and is used for introducing fluid onto the surface area of the object. Also, a sensor is present and is used for indicating the presence of pooling on the surface area of the object.

20 Claims, 4 Drawing Sheets

U.S. PATENT DOCUMENTS

| | | | |
|---|---|---|---|
| 6,215,038 B1 * | 4/2001 | Davis et al. | 604/367 |
| 6,217,890 B1 * | 4/2001 | Paul et al. | 424/402 |
| 6,230,574 B1 | 5/2001 | Rider et al. | |
| 6,238,379 B1 | 5/2001 | Keuhn, Jr. et al. | |
| 6,287,286 B1 | 9/2001 | Akin et al. | |
| 6,296,862 B1 | 10/2001 | Paul et al. | |
| 6,316,013 B1 | 11/2001 | Paul et al. | |
| 6,446,495 B1 * | 9/2002 | Herrlein et al. | 73/73 |
| 6,608,237 B1 * | 8/2003 | Li et al. | 604/382 |
| 2001/0002541 A1 * | 6/2001 | Patel et al. | 62/259.2 |
| 2001/0039405 A1 * | 11/2001 | Keuhn et al. | 604/360 |
| 2002/0120410 A1 * | 8/2002 | Pourdeyhimi | 702/30 |
| 2002/0145525 A1 * | 10/2002 | Friedman et al. | 340/573.5 |
| 2003/0011479 A1 * | 1/2003 | Bluteau | 340/573.5 |
| 2003/0020615 A1 * | 1/2003 | Zand et al. | 340/573.5 |
| 2003/0097113 A1 * | 5/2003 | Molee | 604/385.101 |
| 2004/0064114 A1 * | 4/2004 | David et al. | 604/361 |

FOREIGN PATENT DOCUMENTS

| | | |
|---|---|---|
| FR | 2680678 A1 * | 3/1993 |
| WO | WO8500914 | 2/1985 |
| WO | WO9616389 | 5/1996 |
| WO | WO9858606 | 12/1998 |
| WO | WO9858609 | 12/1998 |
| WO | WO9908259 | 2/1999 |
| WO | WO9929384 | 6/1999 |
| WO | WO9960972 | 12/1999 |
| WO | WO9960974 | 12/1999 |
| WO | WO0197734 | 12/2001 |
| WO | WO0214831 | 2/2002 |

\* cited by examiner

STANDING POSITION

| SAMPLE | TYPE | SAM:FLUFF RATIO | SURGE SIZE (INxIN) | POOLING LOCATION | PERCENTAGE OF OCCURRENCE | AMOUNT BEFORE POOLING (ml) | POOLING TIME(S) |
|---|---|---|---|---|---|---|---|
| #1 | EXPERIMENTAL | 60:40 | 2.5 x 6.5 | THIGH<br>BACK WAIST | 60%<br>40% | 101.9<br>264.1 | 17.2<br>4.1 |
| #2 | EXPERIMENTAL | 40:60 | 2.5 x 6.5 | THIGH<br>BACK WAIST | 60%<br>40% | 114.4<br>266.5 | 9.9<br>9.3 |
| ULTRATRIM | COMMERCIAL | 44:56 | 3.0 x 7.5 | THIGH<br>BACK WAIST | 50%<br>50% | 113.5<br>200.0 | 59.1<br>14.3 |

SUPINE POSITION

| SAMPLE | TYPE | SAM:FLUFF RATIO | SURGE SIZE (INxIN) | POOLING LOCATION | PERCENTAGE OF OCCURRENCE | AMOUNT BEFORE POOLING (ml) | POOLING TIME(S) |
|---|---|---|---|---|---|---|---|
| #1 | EXPERIMENTAL | 60:40 | 2.5 x 6.5 | BUTTOCK<br>BACK WAIST | 80%<br>20% | 104.9<br>9.7 | 27.8 ~ > 600<br>1.4 |
| #2 | EXPERIMENTAL | 40:60 | 2.5 x 6.5 | BUTTOCK<br>BACK WAIST | 90%<br>10% | 42.6<br>3.0 | 98.0 ~ > 600<br>1.3 |
| ULTRATRIM | COMMERCIAL | 44:56 | 3.0 x 7.5 | BUTTOCK | 100% | 60.8 | > 600 |

PRONE POSITION

| SAMPLE | TYPE | SAM:FLUFF RATIO | SURGE SIZE (INxIN) | POOLING LOCATION | PERCENTAGE OF OCCURRENCE | AMOUNT BEFORE POOLING (ml) | POOLING TIME(S) |
|---|---|---|---|---|---|---|---|
| #1 | EXPERIMENTAL | 60:40 | 2.5 x 6.5 | TUMMY<br>THIGH | 80%<br>20% | 102.1<br>22.6 | > 600<br>33.9 |
| #2 | EXPERIMENTAL | 40:60 | 2.5 x 6.5 | TUMMY<br>THIGH | 90%<br>10% | 71.7<br>75.0 | > 600<br>40.2 |
| ULTRATRIM | COMMERCIAL | 44:56 | 3.0 x 7.5 | TUMMY<br>THIGH | 70%<br>30% | 106.0<br>95.7 | > 600<br>61.5 |

FIG.4

METHOD AND APPARATUS OF DETECTING POOLING OF FLUID IN DISPOSABLE OR NON-DISPOSABLE ABSORBENT ARTICLES

BACKGROUND

Absorbent garments such as disposable diapers, adult incontinence garments, sanitary towels, training pants, and other absorbent articles are well known in the art. A disposable absorbent article is typically composed of a top layer that is adjacent to the users body and which allows liquid to move there through. A back layer is also provided that faces the clothing of the user. The back layer does not allow liquid to be transferred from the inside of the absorbent article onto the users clothing. Absorbent materials are located between the top layer and the bottom layer. The absorbent material is configured to absorb liquid and hence help to keep the skin dry.

During normal operation it is therefore the case that fluid is discharged from a user and will subsequently flow through the top layer and be absorbed by the absorbent material. The absorbent material is designed to absorb, redistribute, and store the fluid until the absorbent article is discarded. In some instances, however, fluid may come back from the absorbent material and once again contact the users skin. Such a result would occur for instance if the absorbent material were forced in a certain direction by the weight of the user, or in another instance where due to the amount and orientation of the user the fluid can not be properly absorbed. Such a result is not desired because this liquid can result in over hydration of the contacted skin and in turn create a greater chance of skin irritation for the user. In addition to simply being an irritant, excessive moisture on the skin of a user can cause, among other things, the growth of microorganisms which can undesirably lead to the onset of rashes or infection.

Tests for measuring the performance of absorbent articles have been conducted in the past. Typically the purpose of these tests were to detect early leakage of fluid from absorbent articles. Such tests consisted of constructing an apparatus which resembled a human body. The absorbent article was placed thereon. The apparatus was designed to automatically deliver a specific amount of fluid to the absorbent article. Sensors in the mannequin helped determine the location of leakage, and timers were used to record the elapsed time between the fluid dispensing and the leakage. These tests and methods treat all of the absorbent articles with the same amount of fluid. This resulted in some cases in no difference in performance between the absorbent articles. The purpose of these tests were to detect leakage outside of the absorbent article, and not to determine the location and presence of pooling within the absorbent article and on the users skin.

Other methods measure the humidity within the absorbent article. This humidity can also result in relatively high skin hydration levels, and as previously mentioned foster the growth of microorganisms within the absorbent article. Such methods make use of a hygrometer which is placed within the absorbent article or between the absorbent article and the skin in order to assess the relative humidity within the absorbent article.

It is therefore desirable to provide a method and apparatus for investigating the fluid absorption behavior of absorbent articles relative to the health and wellness of the skin that is surrounded by the articles. It is expected that the results from such a method and apparatus will aide in the design of absorbent articles which demonstrate improved leakage ability and also help to maintain the health and wellness of the skin contacted by those articles.

It is undesirable to have the portion of the absorbent article that contacts the user be wet since it means that that portion of the skin that contacts the absorbent article will also be wet. As defined herein, pooling is defined as occurring when a surface is wet. Pooling occurs when the skin of the user becomes wet. Of course, this is an undesirable situation whether it occurs for a short or a long period of time. In addition to its health consequences, pooling is also undesirable for the reason that it is uncomfortable to the user. It is therefore the case that it would be beneficial to develop a method and an apparatus to detect the location of pooling and the location of absence of pooling in designing absorbent articles such as diapers, adult incontinence articles, feminine products, and the like. Such a method and apparatus would also be beneficial in helping to design these products in order to reduce leakage and to help maintain healthy skin of the user.

SUMMARY

Various features and advantages of the invention will be set forth in part in the following description, or may be obvious from the description, or may be learned from practice of the invention.

The present invention provides for an apparatus that is used for detecting pooling and the absence of pooling. The apparatus includes an object that has at least one surface onto which pooling may occur. A fluid delivery apparatus is present and its purpose is to introduce fluid onto the surface area of the object. A sensor is present for indicating the presence of pooling on the surface area of the object.

In other exemplary embodiments of the present invention, the object may be a lower-torso mannequin. Additionally, the sensors may each comprise two conductive electrodes, which indicate the presence of pooling when the surface area between the electrodes becomes wet. The sensors may be placed at various locations on the lower-torso mannequin. For instance, the sensors may be placed at the front waist, stomach, crotch, leg joint, left thigh, right thigh, buttocks, and/or the back waist of the lower-torso mannequin.

The present invention also encompasses a method for detecting pooling on an object. The method includes the step of providing an object that has at least one surface area onto which pooling occurs. The object may be at least partially surrounded by an absorbent article. The surface area of the object is wetted with a fluid. The presence of pooling of the fluid on the surface area of the object is detected. In an alternative exemplary embodiment of the present invention, the wetting of the surface area is stopped once pooling is detected. Additionally, the time of pooling may be recorded. The time of pooling is defined as being the time interval between the detection of the presence of pooling and the detection of the absence of pooling.

The present apparatus and method may be employed in using absorbent articles that are disposable diapers, disposable adult incontinence products, and/or disposable feminine products. The fluid that is dispensed onto the object may be a 0.9% sodium chloride solution or any conductive fluid or substance.

BRIEF DESCRIPTION OF THE DRAWINGS

FIG. 4 is a table of results obtained from various experiments in locating pooling on a lower-torso mannequin in accordance with one exemplary embodiment of the present invention.

DETAILED DESCRIPTION

Figure 1:
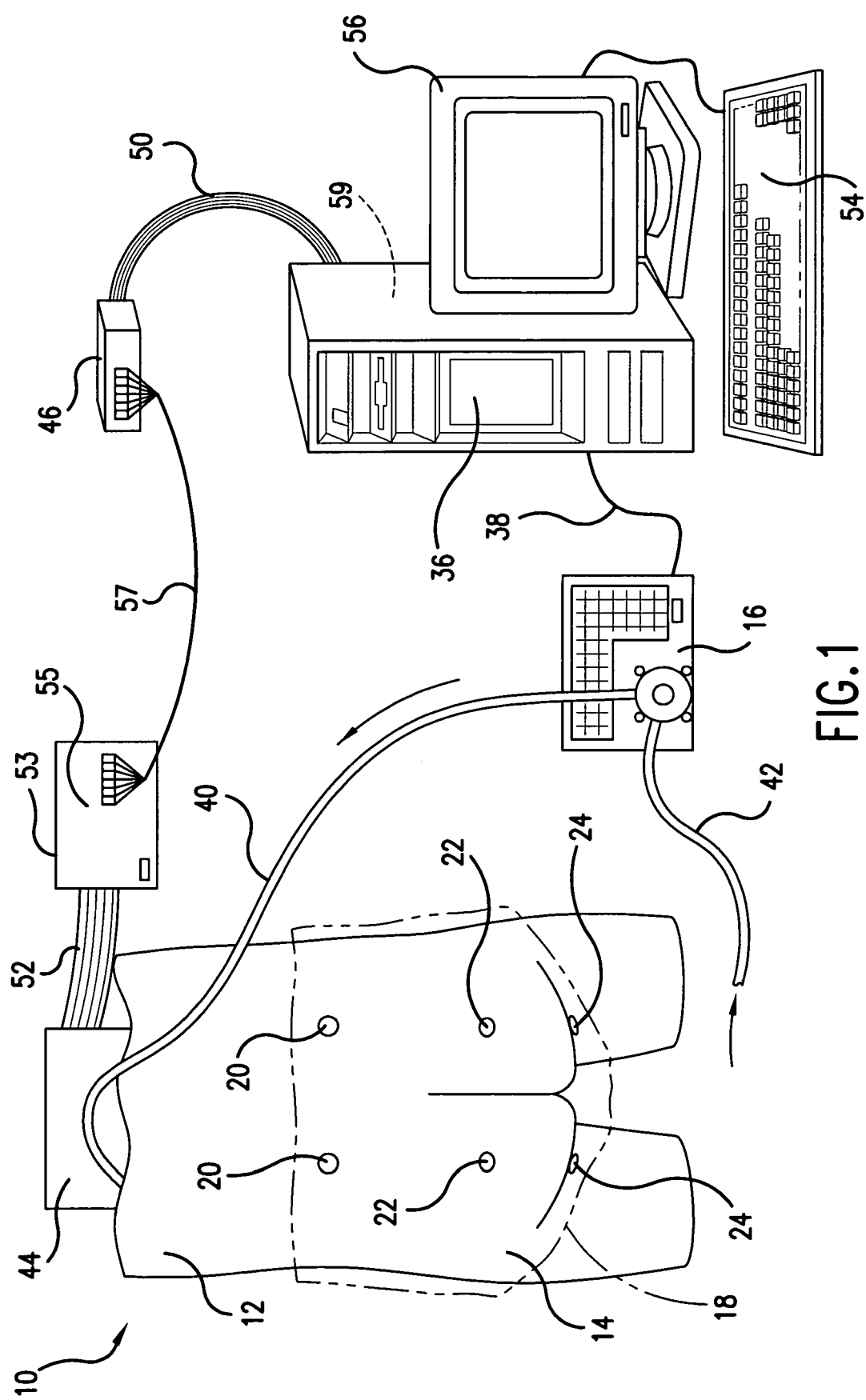
FIG. 1 is a view of an exemplary embodiment of an apparatus for detecting pooling in accordance with the present invention. The drawing shows a back view of a lower-torso mannequin being connected to a fluid delivery apparatus, also shown is a monitoring device with a computer.

Reference will now be made in detail to embodiments of the invention, one or more examples of which are illustrated in the drawings. Each example is provided by way of explanation of the invention, and is not meant as a limitation of the invention. For example, features illustrated or described as part of one embodiment can be used with another embodiment to yield still a third embodiment. It is intended that the present invention include these and other modifications and variations.

Referring now to the drawings, FIG. 1 to the drawings, FIG. 1 shows an apparatus 10 for detecting pooling and the absence of pooling in accordance with the present invention. The apparatus 10 is composed of an object 12 from which pooling may be detected. The object 12 shown in FIG. 1 is a lower-torso mannequin. However, it is to be understood that various configurations of the object 12 are possible, and the object 12 is not limited to a lower-torso mannequin in the present invention. For instance, the object 12 can be an upper body portion, legs, arms, genital area, and/or head of a mannequin. Additionally, the object 12 may be a full body mannequin. Also, object 12 may be an object other than a human mannequin. For instance, the object 12 may be an animal mannequin, a chair, a bed, or any other type of object. It is to be understood that the scope of the present invention includes objects 12 that are not simply lower-torso mannequins.

FIG. 1 shows a fluid delivery apparatus 16 being connected to the object 12 through a fluid input line 40. The purpose of the fluid delivery apparatus 16 is to introduce a fluid into the object 12 which may then eventually be transferred to the surface area 14 of the object 12. The fluid that is transferred from the fluid delivery apparatus 16 may be of any type in the present invention. In one exemplary embodiment, the fluid is a 0.9% sodium chloride solution that is delivered through the fluid input line 40 into the object 12. A fluid reservoir line 42 may be present which is used to supply fluid to the fluid delivery apparatus 16. The fluid reservoir line 42 or may be run from a fluid reservoir (not shown).

Figure 2:
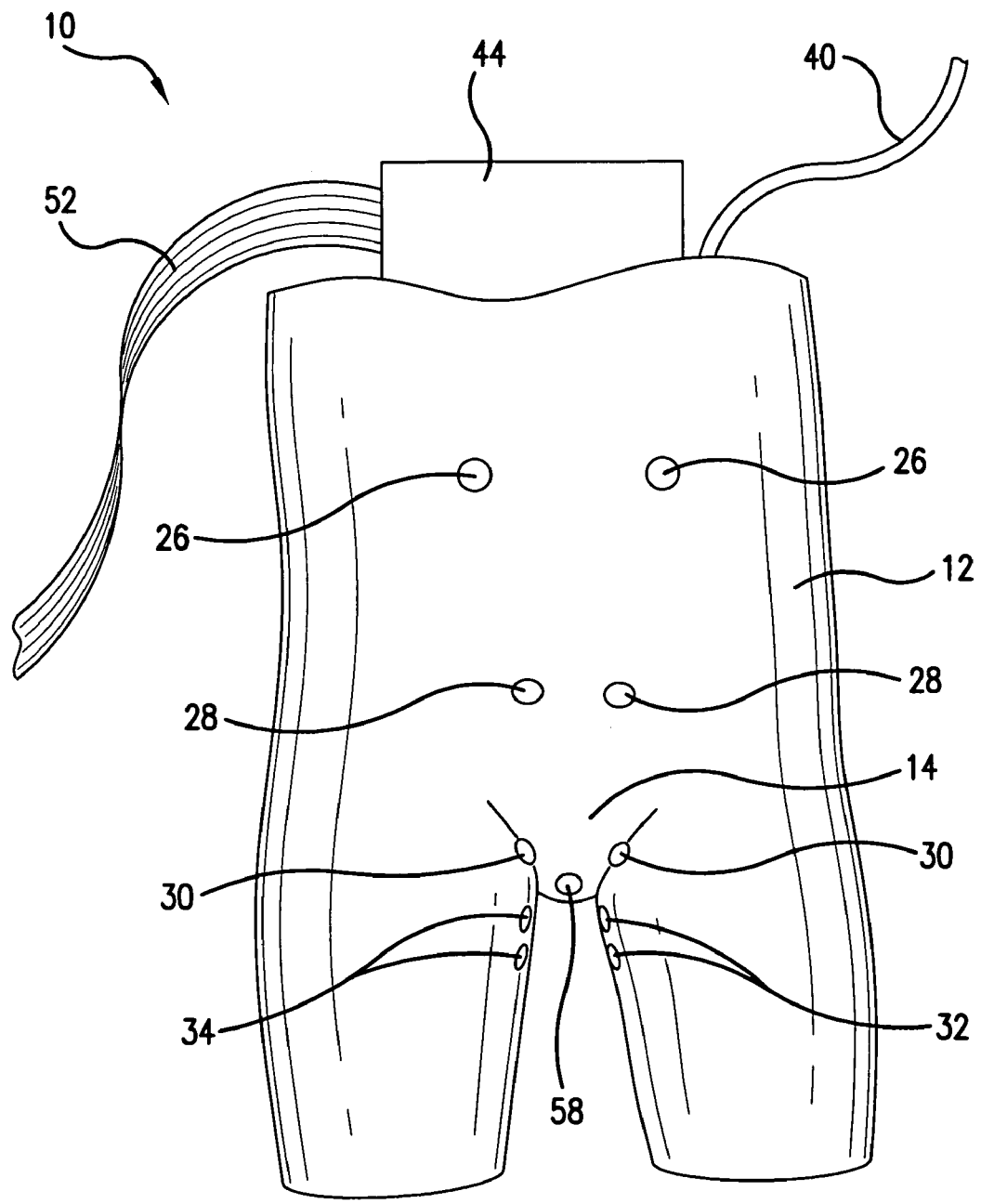
FIG. 2 is a front view of an exemplary embodiment of a lower-torso mannequin. The mannequin has a series of sensors displaced thereon for detecting the presence of pooling on the surface of the mannequin.
Figure 3:
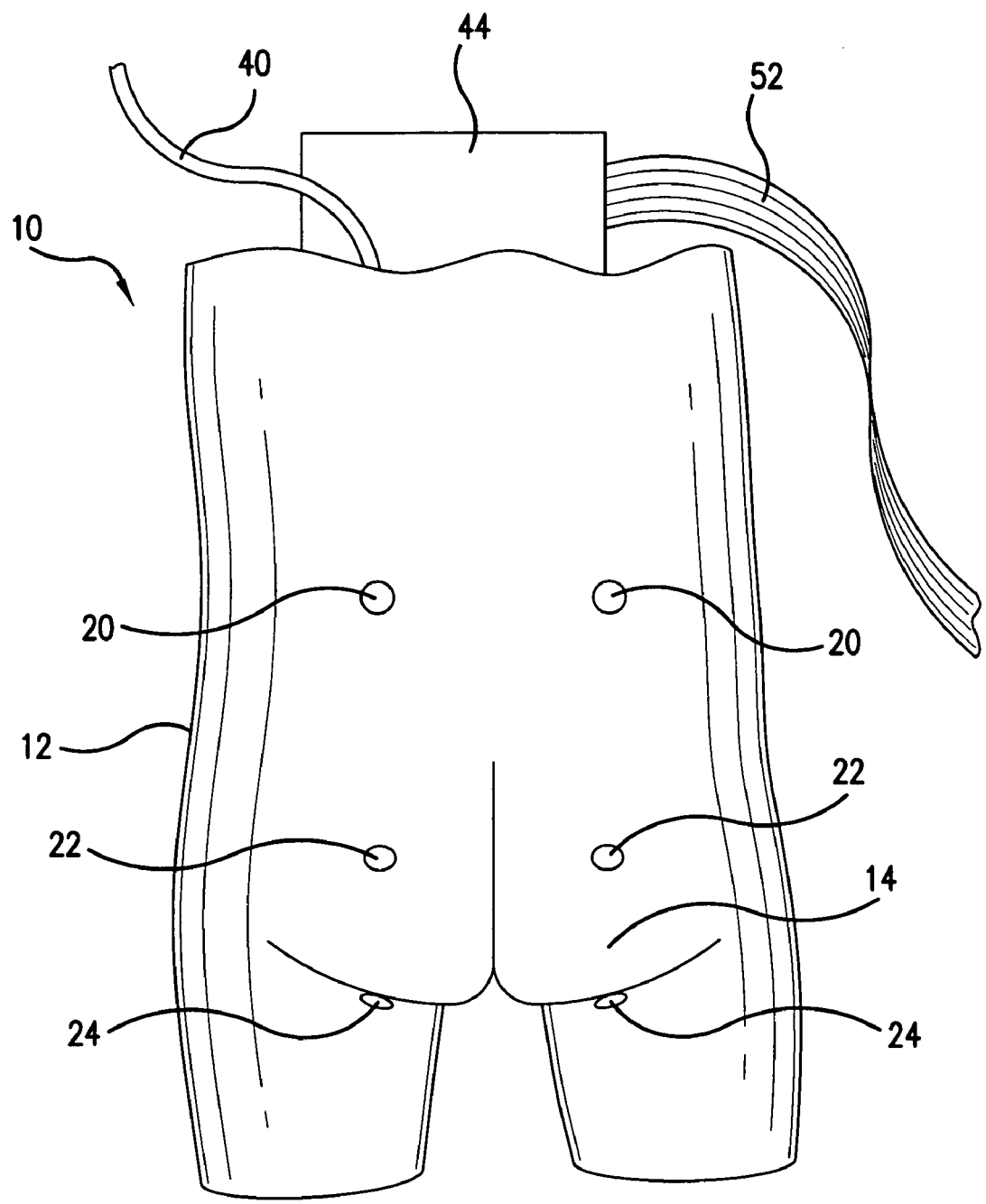
FIG. 3 is a back view of an exemplary embodiment of a lower-torso mannequin in accordance with the present invention. A series of sensors are placed on the surface of the lower-torso mannequin for the purpose of detecting pooling on the surface of the mannequin.

Now referring to FIG. 2, the front side of the object 12 shown in FIG. 1 is presented. As can be seen, the fluid input line 40 enters the top of the object 12, and is embedded within the object 12. Fluid may be dispensed onto the surface area 14 of the object 12 through a fluid insertion port 58 in the surface of the object 12. The fluid insertion port 58 is shaped and positioned in order to simulate the point of urine delivery in an adult or child. However, it is to be understood that under the scope of the present invention, the fluid insertion port 58 may be placed at other locations and may comprise multiple fluid insertion ports 58 as opposed to just a single port. For instance, such multiple insertion ports 58 could be used to simulate sweating of individuals or animals.

Once fluid is dispensed from the fluid insertion port 58, the fluid may then be transferred onto the surface area 14 of the object 12. This fluid transfer is again designed to stimulate the condition where urine or other fluids exit a body and are transferred onto the skin. A series of sensors are positioned on the object 12 to detect the presence and absence of pooling on the object 12. As stated, pooling occurs when the surface of the object 12 becomes wet. The sensors are embedded in a predetermined position within the surface area 14 of the object 12. As can be seen, each sensor is made from two conductive electrodes. For instance, the stomach sensor 26 is made of two electrodes 26, and are located on the stomach section of the object 12.

Other sensors are also located on the front surface of the object 12. As shown in FIG. 2, a pair of front waist sensors 28 are present along with a pair of crotch sensors 30 on the front of the object 12. A pair of left inner thigh sensors 32 are present and are located approximate to one of the crotch sensors 30. Additionally, a pair of right inner thigh sensors 34 are also present and are again positioned close to one of the crotch sensors 30.

Referring back to FIG. 1, additional sensors are shown on the back side of the object 12. A pair of back waist sensors 20 are present on the back waist section of the object 12. Additionally, a pair of buttock sensors 22 along with a pair of leg joint sensors 24 are also present. It is to be understood that the present invention is not limited to placing sensors or a pair of sensors, in the aforementioned positions. It is conceivable under the scope of the present invention that a single sensor may be used instead of a pair of sensors.

Various types of sensors may be employed, for instance electrodes, transducers, photoelectric cells, or cameras may be used as a sensing element in the present invention. Therefore, other sensing elements besides electrodes may be used to determine pooling. Also, more than one or two electrodes or sensing elements may be used to determine pooling at various regions of the surface. For instance, three may be used in other embodiments as opposed to a pair of or a single electrode. Additionally, the electrodes may be of various types, some sensitive to the slightest electrical current while others require a stronger electrical current to pick up a signal. Additionally, the sensors can be-placed at other portions of the object 12 besides those previously mentioned. Additionally, fewer or more than the eight pairs of sensors described may be employed. For instance, it may be desired that a single sensor is placed on the front of the object along with a single sensor being located on the back of the object. The present invention is not limited to the particular number or placement of sensors on the object 12.

An absorbent article 18 (shown in phantom lines) may be placed around the object 12. In the case where the object 12 is a mannequin, such an absorbent article 18 may be a disposable or non-disposable diaper, a disposable or non-disposable incontinence product, or a disposable or non-disposable feminine product. The apparatus 10 may be configured in order to simulate the conditions present in such an absorbent article 18 and on the skin of the user when urine or other fluids are released by the user.

The sensors, for example the back waste sensor 20, may detect fluid there between because the fluid has not yet been absorbed by the absorbent article 18. Fluid detection by the sensor 20 can also be due to fluid which gets squeezed back from the absorbent article 18 onto the surface area 14 due to compression of the absorbent article 18. The presence of pooling also means that it is possible for this fluid to freely migrate on the surface area 14 and possibly leave the absorbent article 18. If fluid migrates out of the absorbent article 18, leakage results. In addition to detecting the presence of pooling on the surface area 14, the sensors 20 may also detect the absence of pooling on the surface area 14.

In one exemplary embodiment, a pair of conductive electrodes 20 are used in which one electrode emits a small electrical current therefrom which is only strong enough to be detected by the other. This detection occurs when a fluid is present. The fluid acts as an electrical conduit and has a higher conductivity than the surface of the mannequin 12. The electrical current may then move through this fluid into the other electrode. This causes completion of an electrical circuit that may be detected by corresponding machinery to indicate the presence of pooling. Of course, other arrangements of detecting the presence of fluid on the mannequin 12 are possible as is known in the art, and the present invention is not limited to the previously described method.

Each pair of sensors, for example the back waist sensors 20, may be made of conductive electrodes. When fluid or wet material from the absorbent article 18 is present between these two electrodes, the circuitry is completed and a signal is generated. Input from all of the sensors (20, 22, 24, 26, 28, 30, 32, and 34) are tied into a sensor manifold 44 at the top of the object 12. Output from the sensor manifold 44 is transferred through a multi-conductor cable 52 to a sensing device 53 containing the fluid sensing circuitry 55. The signals are then brought through another multi-conductor cable 57 to a shielded I/O connector block 46 before being sent to a multifunction 110 board 59 located inside a computer 36 through a shielded 110 cable 50. Although shown as being on the top of the object 12 in the figures, the sensor manifold 44 along with the fluid input line 40 and the multi-conductor cable 52, it is possible to reconfigure the apparatus 10 such that one or more components are situated at different portion of the object 12. The sensing device 53 is capable of detecting the electrical current through the sensors and the conductive substances. The signal sent from the back waist sensor 20 may be a binary signal, which is used to indicate pooling. A binary signal indicates a "yes" or "no" condition. As such, a binary signal would indicate whether fluid "was" or "was not" present. However, in other exemplary embodiments of the present invention, the signal may be one other than binary.

For instance, the signal sent may be a current that has a certain level of electric charge per unit of time. This amount may be detected by corresponding machinery in order to determine not only the presence, but the severity of the pooling. If a strong signal were detected, this could mean an increased amount of pooling is present and vice versa. Of course, in other exemplary embodiments of the present invention, different supporting electronics may be employed. For instance, the sensors may be configured to have their output directly transferred to a computer 36 for processing. The present invention is not limited to the exemplary embodiments shown in FIG. 1 in so far as the apparatus 10 always requiring a connector block 46, a sensing device 53, and cables 50, 52, and 57. In other exemplary embodiments, wireless transfer of information is employed. Additionally, the use of a computer 36 to process and record information is not necessary.

The computer 36 is provided with a keyboard 54 and a monitor 56 in order to interface with a person conducting the test. In one exemplary embodiment of the present invention, when the interfaced computer 36 receives a signal from the sensors which indicates pooling, the computer 36 sends a signal to the fluid delivery apparatus 16 through a communication line 38 in order to stop the delivery of fluid to the object 12. When this occurs, pooling is now present on the surface area 14 of the object 12, and the computer 36 begins the recordation of the time of pooling. Once the pooling becomes absent, for instance it is absorbed by the absorbent article 18 and drawn off of the surface area 14, the signal from the sensors, for example the back waist sensor 20, is no longer present. At this point, when the pooling is absent another time is recorded by the computer 36 to indicate the end of pooling. The difference between the time at the start of pooling and the time at the end of pooling may be defined as the pooling time.

The apparatus 10 may therefore monitor the pooling time at various points on the surface area 14. In addition, the apparatus 10 can also measure the pooling time associated with different amounts of fluid being inputted by the fluid delivery apparatus 16 and eventually present on the surface area 14. This amount of fluid can be measured by setting the fluid delivery apparatus 16 to a given flow rate throughout the running of the test conducted with the apparatus 10. In certain exemplary embodiments of the present invention the amount of fluid delivered to the object 12 and imparted onto the surface area 14 stops when pooling occurs on the surface area 14. However, in other exemplary embodiments of the present invention, the delivery of fluid from the fluid delivery apparatus 16 is not stopped once the presence of pooling is detected. The amount of fluid delivered by the fluid delivery apparatus 16 is therefore dependent on the ability of the absorbent article 18 to distribute and channel the fluid into the fluid storing sections of the absorbent article 18. It is therefore the case that in this type of an arrangement of apparatus 10, the amount of fluid delivered to the object 12 is dependent upon the absorption quality of the absorbent article 18. However, it is to be understood that in other exemplary embodiments of the present invention, the same amount of fluid may be delivered to the object 12 and imparted onto the surface area 14 regardless of the type or quality of the absorbent article 18. By detecting pooling inside the absorbent article 18, one may more clearly understand the effects of pooling on the health of the skin inside of the absorbent article 18 and allow one to more efficiently design an absorbent article 18 that minimizes or reduces pooling.

The results of the apparatus 10 may be displayed on the monitor 56. The results may be shown in any format, for example they may be shown in a tabular format on the monitor 56. Additionally, other ways of displaying the results from the apparatus 10 may be envisioned. For instance, the intensity and the duration of pooling may be displayed in a three dimensional model that has color indicators which indicate the intensity and duration of pooling. As stated, intensity of pooling may be detected in one way by measuring the strength of the current or signal detected when pooling occurs. This modeling and the results derived therefrom could then be used to best locate certain components of the absorbent article 18. For instance these could be the absorbent materials, moisture resistant materials, barrier materials, and other items that may improve the performance of the absorbent article 18 in consumer use.

The apparatus 10 therefore allows for one to monitor the possibility of skin hydration brought about by pooling when absorbent articles 18 are used. Such knowledge is helpful in the design of absorbent systems for diapers, adult incontinence products, and/or feminine products for the purpose of reducing leakage of these products and maintaining healthy skin.

It should be understood that the present invention includes various modifications that can be made to the exemplary embodiments of the method and apparatus of detecting pooling of fluid and disposable absorbent articles as described herein as come within the scope of the appended claims and their equivalents.

Experiment Carried Out on One Exemplary Embodiment of the Present Invention

Referring now to FIG. 4, results derived from experiments conducted in accordance with one exemplary embodiment of the present invention are shown. In these experiments, three different types of diapers were tested on the test arrangement shown in the exemplary embodiment displayed in FIG. 1. In this instance, two experimental diapers and one commercial HUGGIES ULTRATRIM DIAPER® were used. The make up of these two types of diapers are shown in FIG. 4.

Surge size indicates the width and length of a surge layer of the diaper. The surge layer allows for quick absorbtion of fluid into an absorbent core. The absorbent core is made of SAM material which is super absorbent material. Also composing the absorbent core is fluff, which is made of fluff paper product and/or cellulosic fibers. Ratios of these two components, SAM and fluff are shown in the third column of FIG. 4. The object 12 is a lower-torso mannequin, and for each given mannequin position, ten samples of each diaper type were tested. Three positions of the object 12 were used in the experiment. These positions were: standing, supine, and prone, but not limited to any other positions of interest. The flow rate delivered from the fluid delivery apparatus 16 was set at 120 ml/min but not limited to any other rate which is appropriate for the test samples. A 0.9% sodium chloride solution was used as the injection fluid but it is not limited to any other conductive fluid or substances.

In the standing position, it was found that the location of pooling in the diapers either occurs at the thighs or at the back waist of the object 12. The amount of fluid that causes pooling at the thighs is usually smaller than the amount that causes pooling at the back waist. When pooling occurs at the back waist in a standing position, it indicates that the diaper surge layer has worked to distribute the fluid to the absorbent core of the diaper. However, when pooling occurs at the thighs, it implies that leakage may occur since limited absorbent materials are present in the thigh area. In terms of percentage of occurrence, the diapers that have narrower surge layers have a higher percentage of pooling occurring at the thighs.

In the supine position the location of pooling is mainly at the buttocks area for all three types of diapers. However, some occurrence of pooling occurs at the back waist, especially with the diapers that have narrower and shorter surge layers. It was observed that the amount of fluid that causes pooling at the back waist was relatively small when compared to the amount of fluid that causes pooling at the buttocks. In most cases, it is undesirable to have pooling at the back waist when the mannequin is in a supine position. This is because the fluid may migrate out of the diaper more easily to cause leakage. It was also observed in the experiments that when the pooling occurs at the buttocks, the pooling time tends to be long and often exceeds 10 minutes. Such a long pooling time indicates that the surface area 14 of the object 12 remains wet. As stated, this prolong wetness is highly undesirable in a real wear situation since it means that the skin which contacts that portion of the diaper would also remain wet.

In the prone position, the location of pooling is mainly at the stomach area and occasionally at the thighs. Again, the amount of fluid that causes pooling at the thighs is usually much smaller than the amount of fluid that causes pooling at the stomach. When pooling occurs at the stomach, it means that the surge layer has distributed the fluid to the designed area. However, such distribution of fluid may not have any advantage to the wellness of the skin in contact with the diaper. It was found that prolonged pooling signals result in the stomach area when the mannequin is in the prone position.

What is claimed is:

1. An apparatus for detecting pooling and absence of pooling comprising:
   an object having at least one surface area onto which pooling can occur, the object comprising a lower-torso mannequin configured for having an absorbent article placed thereon;
   a fluid delivery apparatus for introducing fluid onto said surface area of said object;
   at least two sensors located on said object for indicating the presence of pooling on said surface area of said object, wherein said at least two sensors are located on said object such that said at least two sensors are covered by said absorbent article and can indicate the presence of pooling at different locations on said object; and
   a computer that receives a signal from said sensor that indicates the presence of pooling, said computer configured to cause said fluid delivery apparatus to stop delivering fluid to said surface area of said object, said computer also configured to record the time of pooling.

2. An apparatus for detecting pooling and absence of pooling comprising:
   an object having at least one surface area onto which pooling can occur, the object comprising a lower-torso mannequin configured for having an absorbent article placed thereon;
   a fluid delivery apparatus for introducing fluid onto said surface area of said object; and
   at least two sensors located on said object for indicating the presence of pooling on said surface area of said object, wherein said at least two sensors are located on said object such that said at least two sensors are covered by said absorbent article, and wherein said at least two sensors are located at different locations on said object in order to indicate the presence of pooling at different locations on said object.

3. The apparatus as set forth in claim 1, further comprising an absorbent article at least partially surrounding said object and configured for absorbing the fluid from said surface area of said object, and wherein the absorbent article is selected from the group consisting of disposable or non-disposable diapers, disposable or non-disposable adult incontinence products, and disposable or non-disposable feminine products.

4. The apparatus as set forth in claim 1, wherein said at least two sensors each comprise two conductive electrodes.

5. The apparatus as set forth in claim 1, wherein said fluid delivery apparatus comprises a computer controlled pump in communication with embedded tubing within said object.

6. An apparatus for detecting pooling and absence of pooling comprising:

an object having at least one surface area onto which pooling can occur, wherein said object comprises a lower-torso mannequin configured for placing an absorbent article thereof;

a fluid delivery apparatus for introducing fluid onto said surface area of said object; and at least eight sensors for indicating the presence of pooling on said surface area of said object, wherein at least eight sensors are present and are located on said object such that said sensors are covered by said absorbent article when placed thereof, wherein one of said at least eight sensors being located at least at the front waist, stomach, crotch, leg joint, left thigh, right thigh, buttock, and back waist of said lower-torso mannequin, wherein said sensors are used to indicate the presence of pooling at different locations on said lower-torso mannequin.

7. A method for detecting pooling on the surface of a lower-torso mannequin, comprising;

providing a lower-torso mannequin having a plurality of sensors located on the surface of said lower-torso mannequin, wherein said plurality of sensor are located on said object such that said plurality of sensors are covered by an absorbent article placed on said object, and wherein said sensors are located in at least two different locations on the surface of said lower-torso mannequin;

providing a computer in communication with said plurality of sensors;

at least partially covering said lower-torso mannequin with an absorbent article;

introducing fluid onto the surface of said lower-torso mannequin;

detecting pooling on the surface of said lower-torso mannequin;

detecting the absence of pooling on the surface of said lower-torso mannequin;

calculating with said computer the pooling time by taking the time difference between the detection of pooling and the absence of pooling; and determining the location of pooling with the use of said computer.

8. The method of detecting pooling on the surface of a lower-torso mannequin as set forth in claim 7, further comprising the step of stopping the introduction of fluid once pooling is detected.

9. The method of detecting pooling on the surface of a lower-torso mannequin of claim 7, further comprising the step of adjusting the structure of said absorbent article based on results from said step of calculating pooling time.

10. The method of detecting pooling on the surface of a lower-torso mannequin of claim 7, further comprising the step of calculating the amount of fluid introduced onto the surface before pooling is detected.

11. A method for detecting pooling on an object comprising:

providing an object having at least one surface area onto which pooling occurs and being at least partially surrounded by an absorbent article, wherein said object comprises a lower-torso mannequin;

locating sensors on said object in at least two different locations on the surface of said object to be covered by the absorbent article;

providing a computer in communication with said sensors;

wetting said surface area of said object with a fluid; and detecting the presence of pooling of the fluid on said surface area of said object; and determining the location of pooling with the use of said computer.

12. The method as set forth in claim 11, further comprising the step of detecting the absence of pooling of the fluid on said surface area of said object.

13. The method as set forth in claim 12, further comprising the step of stopping said wetting of said surface area once pooling is detected.

14. The method as set forth in claim 13, further comprising the step of recording the time of pooling as being the time interval between said detection of the presence of pooling, after said stopping of wetting said surface area, and said detection of the absence of pooling.

15. The method as set forth in claim 11, wherein said step of detecting the presence of pooling of the fluid is accomplished by a sensor having two conductive electrodes which detect completion of a circuit when fluid or a section of wet absorbent article is therebetween.

16. The method as set forth in claim 11, wherein said absorbent article is selected from the group consisting of disposable or non-disposable diapers, disposable or non-disposable adult incontinence products, and disposable or non-disposable feminine products.

17. The method as set forth in claim 16, wherein said step of detecting the presence of pooling occurs at one or more locations selected from the group consisting of the front, waist, stomach, crotch, leg joint, left thigh, right thigh, buttock, and back waist of said lower-torso mannequin.

18. The method as set forth in claim 14, further comprising the step of reporting the intensity and duration of pooling in a computer generated display in a three dimensional model having color indicators to indicate the intensity and duration of pooling.

19. The method as set forth in claim 11, wherein the fluid is a 0.9% sodium chloride solution.

20. The method as set forth in claim 11, further comprising the step of calculating the amount of fluid applied to said surface area of said object before pooling is detected.

* * * * *